United States Patent [19]

Esmon et al.

[11] Patent Number: 5,147,779
[45] Date of Patent: Sep. 15, 1992

[54] METHOD FOR EVALUATING IMMUNOGENICITY

[75] Inventors: Pamela C. Esmon, Richmond; Michael A. Fournel, Castro Valley, both of Calif.

[73] Assignee: Miles Inc., Elkhart, Ind.

[21] Appl. No.: 202,177

[22] Filed: Jun. 1, 1988

[51] Int. Cl.⁵ .................. C12Q 1/68; G01N 33/543
[52] U.S. Cl. ..................................... 435/6; 436/518; 436/530; 436/532; 436/547; 436/824; 424/9; 424/85.8; 530/413
[58] Field of Search ............... 436/518, 530, 528, 529, 436/532; 530/387, 413; 435/6; 424/85.8, 88

[56] References Cited

U.S. PATENT DOCUMENTS 4,746,647  5/1988  Svenson ............................. 514/3
4,769,320  9/1988  Furie et al. ......................... 435/7

OTHER PUBLICATIONS

Ritchie "Preparation of Polyclonal Antisera" Chapter 2, Manual of Clinical Laboratory Immunology 1986 pp. 4–8.
Voller et al. "Enzyme-Linked Immunosorbent Assay" Chapter 17, Manual of Clinical Laboratory Immunology 1986 pp. 99, 103–104.
Smith et al. "Monoclonal Antibody Screening: Two Methods Using Antigens Immobilized on Nitrocellulose" Analytical Biochemistry 138 (1984) pp. 119–124.
Esmon P. C., Mitra I., Fournel M. A. 1988; Recombinant Factor VIII Immunogenicity studies. FASEBJ 2(5)5027.

Primary Examiner—Esther L. Kepplinger
Assistant Examiner—Carol E. Bidwell
Attorney, Agent, or Firm—David Aston; James A. Giblin; Elizabeth F. Enayati

[57] ABSTRACT

A method for evaluating the potential immunogenicity of a protein derived from recombinant DNA technology. The method involves injecting an animal with the recombinant protein and then isolating antiserum from the animal. The antiserum is depleted of antibodies to a reference protein, i.e., a plasma derived protein, by adsorbing the antiserum against the reference protein. The adsorbed antiserum is then blotted against the recombinant protein, to see if any antibodies were produced which recognize the recombinant protein, but did not recognize the plasma-derived protein during adsorption.

8 Claims, 3 Drawing Sheets

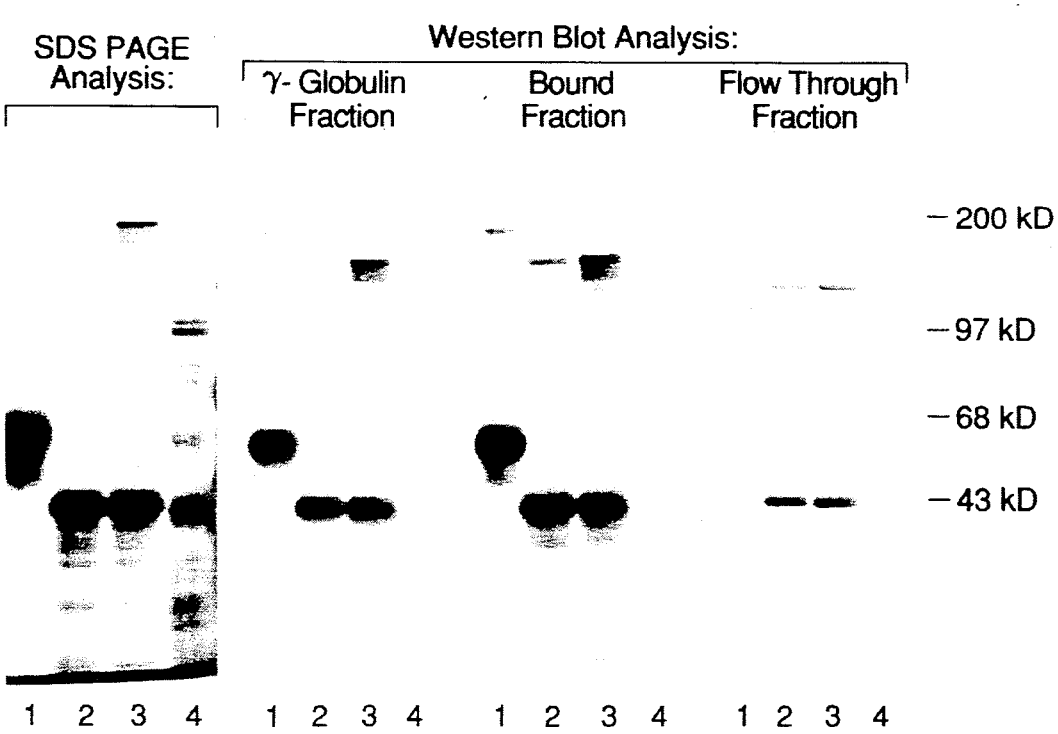
FIG._1

FIG._2

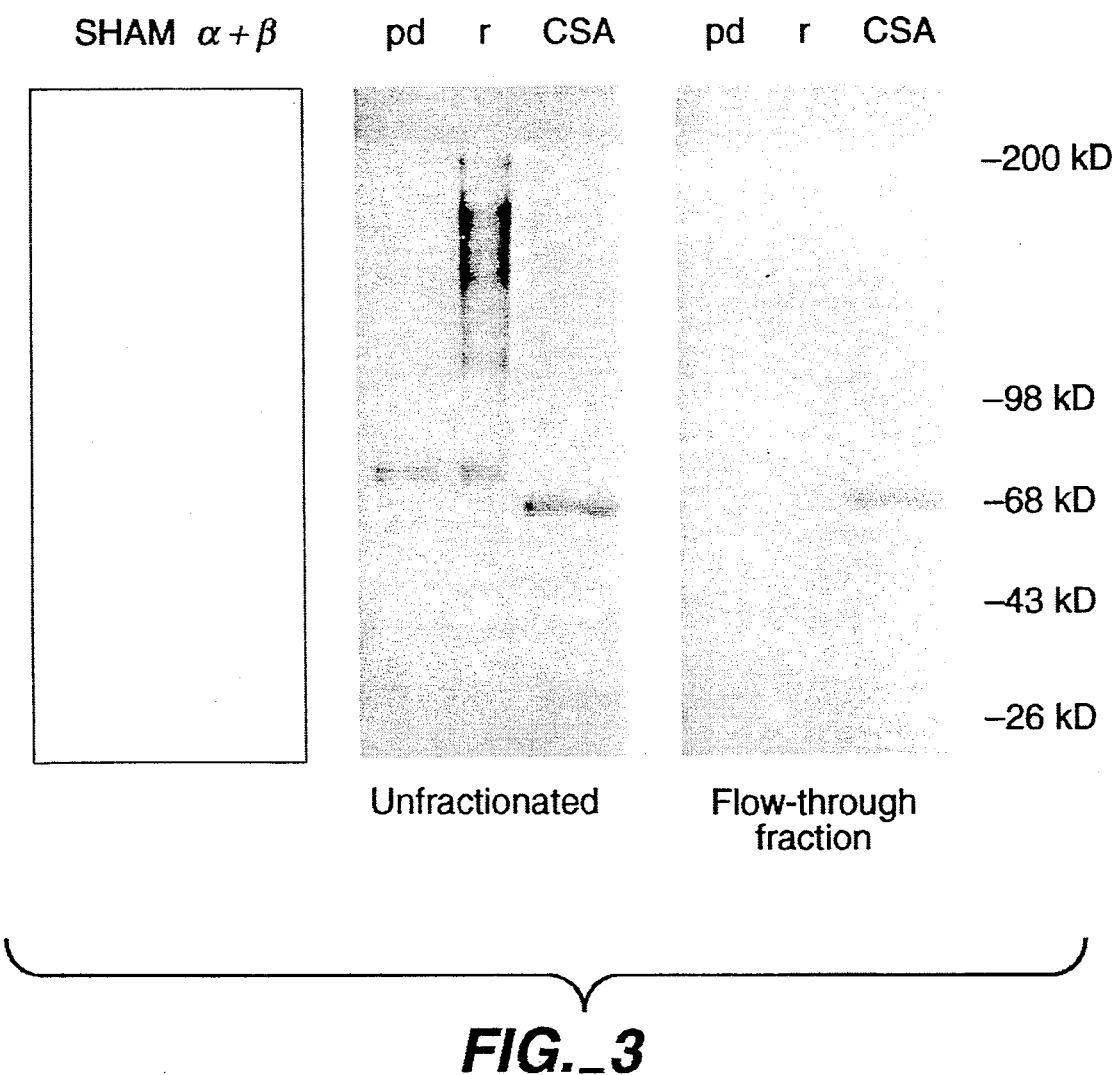
FIG._3

METHOD FOR EVALUATING IMMUNOGENICITY

BACKGROUND OF THE INVENTION

1. Field of the Invention

The present invention relates to the preclinical testing of therapeutic products and, more particularly, to the testing of a protein, intended for repeated administration in humans, for immunogenicity through the use of a protocol involving the use of the immune system of an animal and the comparison of immune responses to a test and a reference protein.

2. Description of the Related Art

With the advent of recombinant DNA technology, a number of therapeutically active peptides have been developed for use in humans. These peptides are coded for by human genes which have been cloned into a host system for production. The host system may be a bacterium, such as *E. coli*, a yeast such as *Saccharomyces cerevisae*, or a mammalian cell line, such as a hybridoma or a continuous cell line such as Chinese Hamster Ovary or Baby Hamster Kidney.

Regardless of the host system chosen, there are questions which may be raised as to the "authenticity" of a peptide product, in terms of its suitability for human use. One such question involves the response of an immunocompetent human host to the therapeutic peptide. This response may in certain instances have clinical significance, such as has been reported in some cases of administration of recombinant human growth hormone (produced in *E. coli*) or in the case of murine monoclonal antibodies. Unfortunately, the human immune response to a therapeutic peptide is impossible to predict with certainty, and little literature exists on the development of animal models which can be used to predict immunogenicity in preclinical testing.

One method which has been previously used by developers of therapeutic peptides is to simply administer to animals repeated injections of the protein of interest and observe clinical signs. This method has several substantial drawbacks. First, it is expected that all peptides beyond approximately 5kD will elicit an immune response in a non-homologous species. Therefore, the appearance of antibodies in such a protocol is to be expected. The mere quantification of these antibodies is not particularly informative, since comparisons among different peptides and different animals are not meaningful.

A common method of immunogenicity testing in animals involves repeat administration of final container product and subsequent animal evaluation. Such evaluation may range from observation for anaphylactic reactions to measurement of immune complexes.

Another methodology of relevance is passive cutaneous anaphylaxis (PCA), although this test method is not particularly used for immunogenicity testing per se. This is because it is a passive system and does not measure immune response. In this system, an antibody is administered to a guinea pig intracutaneously. Then, an antigen of interest is administered intravenously, coupled with a blue dye.

If antigen-antibody complexes are formed, the complexes and the dye will be extravacised, leading to blue spot(s) at the injection site(s). This method is further described by Ovary, Z. (1958).

A chemotactic assay for immunogenicity is described in U.S. Pat. No. 4,714,674.

SUMMARY OF THE INVENTION

The present invention provides a method for evaluating the immunogenicity of a therapeutic product prior to its use in humans.

The method is particularly well suited for use with therapeutic proteins. The protein of interest, termed herein "PX", for unknown protein or product, is compared to a naturally occurring counterpart, termed herein "PR", for reference product. For example, PX may be recombinant alpha-1-proteinase inhibitor or recombinant Factor VIII and PR may be plasma derived alpha-1-proteinase inhibitor or plasma derived Factor VIII, respectively.

PX is purified and injected into an animal so that the animal raises antibodies to PX. The rabbit has been found to be particularly well suited for this purpose, as it has a particularly sensitive immune system. The rabbit antiserum is then isolated and adsorbed against PR.

The adsorption protocol has been found to be particularly effective according to the following steps: The PR is coupled to a solid support i.e., a column. The IgG purified from the antiserum is passed over the solid support so that all antibodies to PR in the antiserum are bound to the PR in the support. The adsorbed antibody is tested against PR to verify that no reactivity towards PR remains.

The adsorbed antibody is also tested against PX. This is done according to the Western Blotting procedure in parallel with the testing against PR. The antibody should show no reactivity with PR, due to the previous adsorption. Any reactivity of the antibody with PX indicates that the animal has produced antibodies against PX which recognize a different epitope on PX than any epitope on PR, otherwise the antibody would have been adsorbed by PR. This means that there exist on PX potentially antigenic sites in comparison to PR, and that the candidate product should be considered as potentially immunogenic in humans. Data have been developed and are presented herein which show both positive and negative results in terms of potential immunogenicity.

While it is possible to use a plasma-derived protein as the immunizing protein, (i.e., PX) it is important to recognize that this would show whether or not there exist epitopes on the plasma-derived protein which do not exist in the recombinant protein (i.e., PR). This is not per se a relevant inquiry in terms of potential immunogenicity in humans.

Furthermore, the present method may employ a panel of monoclonal antibodies in lieu of a polyclonal antibody.

BRIEF DESCRIPTION OF THE DRAWING

FIG. 1 is an SDS-PAGE and a Western Blot Analysis of plasma derived and recombinant Alpha-1-proteinase inhibitor, 1 $\mu$g protein was applied to each lane;

FIG. 2 is a Silver Stained SDS-PAGE Analysis of plasma-derived (pd) and recombinant (r) Factor VIII, with chicken serum albumin (CSA) used as a control; and FIG. 3 is a Western Blot of Factor VIII done on SDS-PAGE. Filters were probed with the indicated antibody as described below. Protein per lane: 1 $\mu$g rFVIII, 1 $\mu$g chicken serum albumin, 10 $\mu$g SHAM 3

(Host cell protein), 10 μg α+β globulin (media protein).

DESCRIPTION OF THE PREFERRED EMBODIMENT

Alpha-1-Proteinase Inhibitor

Alpha-1-Proteinase Inhibitor (Alpha-1-PI; Alpha-1 anti-trypsin) is a 54,000 dalton glycoprotein normally present in human plasma at a concentration of 1.3 mg/mL (Pannell et al, 1974). Individuals with a hereditary deficiency in this neutrophil elastase inhibitor have been shown to have a high disposition for the development of emphysema.

The application of recombinant DNA (rDNA) technology to this protein in recent years has yielded a variety of interesting molecules of potential therapeutic utility. Rosenberg et al (1984) and Courtney et al (1984, 1985) have described the expression of Alpha-1-PI in yeast or E. coli, respectively, and have also described mutant forms of the molecule with biochemical properties distinct from the native form which have potential therapeutic significance.

Such rDNA Alpha-1-PI molecules have sequence homology to the native form but lack of glycosylation (which accounts for 14% of the mass of the plasma-derived molecule). Although the functional significance of carbohydrate in plasma proteins remains unclear, recent evidence has indicated the circulating half-life of non-glycosylated forms of this molecule in animals is substantially shorter than that obtained with the plasma-derived form (Travis et al, 1985).

The present example was undertaken to evaluate the potential immunogenicity of the molecule to determine if unique epitopes might exist in the molecules which lack carbohydrate but are sequentially homologous with the native human plasma molecule.

Materials and Methods

Alpha-1-PI Proteins. rDNA derived Alpha-1-PI was synthesized in yeast as described by Rosenberg et al (1984); both MET358 and VAL358 forms of the molecule were used, i.e. having either a methionine or a valine at amino acid position 358. Subsequent purification was accomplished by methods essentially as described by Janoff et al (1986) and material was stored at +4° C. or frozen until use. Human plasma-derived Alpha-1-PI was initially purified as described by Coan et al (1985) and further purified to homogeneity by the method of Glaser et al (1982); purity of >95% was demonstrated by specific activity and SDS-PAGE analysis.

Alpha-1-PI antigen was quantitated employing a sandwich ELISA technique similar to that described by Revak et al (1985) in which an immunopurified rabbit anti-human Alpha-1-PI antibody was used. F(ab')$_2$ of the antibody was used to coat microtiter wells; once non-specific binding was blocked with bovine serum albumin, test samples were added followed after incubation by intact antibody. Detection was accomplished with a Protein-A-horseradish peroxidase conjugate (Boehringer Mannhein Biochemicals) and addition of a specific colorimetric reagent, 2,2'-azino-di(3-ethylbenzthiazoline sulfonic acid) (ABTS; Sigma), stopping the reaction with 5% sodium dodecyl sulfate; color development quantitation was accomplished in a Dynatech ELISA Reader.

Electrophoresis was performed in 8% polyacrylamide gels with sodium dodecyl sulfate treated samples (SDS-PAGE) according to Laemmli (1970) and stained by the silver nitrate method of Morrissey et al (1981). Western blotting analysis was performed essentially according to Renart et al (1979). Passive cutaneous anaphylaxis assay was performed in guinea pigs as described by Gervoy et al (1977).

Experimental

Polyclonal antisera to both rDNA derived proteins (MET and VAL) and a non-transfected yeast extract were separately raised in groups of three New Zealand White rabbits (2-4 kg, male) by repeated subcutaneous injection of the subject protein emulsified in Freund's complete (initial injection) or incomplete adjuvant. Development of antibody was assessed by precipitin formation in agar gel and harvest of immune serum accomplished. Gamma-globulin fractions were prepared by DEAE-Sepharose ® (Pharmacia) chromatography. Following coupling of human plasma-derived Alpha-1-PI to CNBr-Sepharose (Pharmacia) at a load of 5 mg/mL gel, adsorption of the specific gamma-globulin was accomplished by cycling the respective protein gamma globulin fraction through the column of human Alpha-1-PI-Sepharose in a 5 mM Tris + 0.15 M NaCl buffer, pH 7.4. Specifically bound antibody ("Bound Fraction") was subsequently eluted with 1 M proprionic acid in the Tris-saline buffer, pH 3.5 and collected into solid Tris to return the pH to 7.0-7.4. Cycling in this fashion persisted until no significant A$_{280}$ increase was obtained in the propionic acid elution step. The "Flow Through Fraction" represents antibody that did not bind to the affinity column. All resulting fractions were stored at −20° C. until use.

Antibody raised in rabbits against each rDNA-Alpha-1-PI protein was subjected to repetitive adsorption against plasma-derived Alpha-1-PI immobilized on CNBr-Sepharose, as described above. The resulting antibody fractions were then used to probe nitrocellulose membranes to which had been transferred all three proteins as well as a yeast extract. FIG. 1 presents the results obtained in such an experiment with the rabbit-anti-rDNA-VAL358-Alpha-1-PI antibody fractions.

In FIG. 1, each lane corresponds to the following preparations: (1) plasma derived (pd) Alpha-1-PI; (2) rDNA-MET-Alpha-1-PI; (3) rDNA-VAL-Alpha-1-PI; and (4) yeast extract. Molecular weights are determined from pre-stained markers. The first panel in FIG. 1 represents the SDS PAGE patterns of each sample after silver staining. The second panel represents the Western blot using the gamma globulin fraction of pooled antisera from rabbits, each rabbit having been immunized with rDNA-VAL Alpha-1-PI.

This unfractionated gamma globulin was able to recognize both rDNA proteins and the plasma-derived molecule, including some high molecular weight aggregates; note the absence of recognition of a major yeast extract protein band seen in the SDS-PAGE gel with a molecular weight apparently similar to either rDNA derived Alpha-1-PI protein (mobility difference from plasma-derived Alpha-1-PI presumably due to absence of glycosylation).

The BOUND fraction (third panel) similarly recognizes all three Alpha-1-PI species, but the FLOW THROUGH FRACTION, fourth panel, (i.e., that gamma globulin which did not bind to plasma-derived Alpha-1-PI Sepharose) failed to blot the plasma-derived protein but still quite strongly recognized both rDNA derived Alpha-1-PI molecules (as well as a higher molecular weight yeast extract protein). The recognition of the MET-Alpha-1-PI by this antibody suggests that unique antigen(s) were not due to the single amino acid substitution. Similar results were obtained when rabbit-anti-rDNA-MET358-Alpha-1-PI antibody was subjected to this protocol. These results were also confirmed for both antibody preparations in passive cutaneous anaphylaxis analyses in which significant reaction was seen with either FLOW THROUGH fraction with both rDNA derived Alpha-1-PI proteins but not with plasma-derived Alpha-1-PI.

The present study suggests that if the rabbit could distinguish unique determinants on rDNA derived proteins from the corresponding plasma-derived protein, then it would be likely that a human recipient would also and thus might be expected to generate antibodies against those unique sites (but no shared determinants). The results obtained clearly suggest the presence of such unique epitopes in both rDNA derived proteins, presumably independent of the active site substitutions. While these studies have used adjuvant stimulation and sub-cutaneous inoculation to achieve maximal antibody formation the conclusion that unique determinants apparently exist on either rDNA derived molecule present at least the possibility of a similar recognition in humans.

It should also be noted that the present series of experiments evaluated two different rDNA proteins having single amino acid substitutions. It is contemplated that the present process would also be useful in the evaluation of a protein analogue in reference to a standard or native "reference protein" containing the native amino acid sequence.

Factor VIII

This study was done with recombinant DNA-derived Factor VIII (rFVIII) as described in Vehar et al. "Structure of Human Factor VIII," Nature 312:337-342 (1984) and Eaton et al., "Characterization of Recombinant Human Factor VIII," J. Biol. Chem. 262(7) 3285-3290 (1987). This material is shown in lane 2, FIG. 2, which is a silver-stained 4-12% SDS PAGE. Lane 1 of FIG. 2 contains similar purified plasma derived Factor VIII (pd FVIII). Lane 3 contains a control protein, chicken serum albumin, obtained from Sigma Chemical Co.

To test for the presence of potential immunogenic epitopes in rFVIII, antibody to rFVIII was raised in rabbits as described below. This antibody then was analyzed for antibody that would not cross-react with pdFVIII. To perform this task, rabbit anti-rFVIII (R$\alpha$rFVIII) antibody was first adsorbed using two different affinity columns designed to remove antibody directed toward proteins known to contaminate rFVIII. Antibody to host cell protein contaminants was removed by adsorption against a preparation designated "SHAM 3." SHAM 3 is a protein mixture derived from the culture supernatant of non-FVIII secreting host cells after the supernatant was subjected to the first step in rFVIII purification (i.e., a DEAE column). Antibody to media constituents was similarly removed by adsorption against an $\alpha + \beta$ globulin fraction from media protein supplement.

Antibody Preparation: Groups of three New Zealand White rabbits were immunized subcutaneously with 1 mL of an emulsion of 70 $\mu$g/mL rFVIII plus 7 $\mu$g/mL chicken albumin in Freunds complete adjuvant and were boosted weekly for five weeks with the same antigens in Freunds incomplete adjuvant. After six weeks, plasma was collected and converted to serum. To prepare IgG, serum was diluted 1:3 with distilled water, applied to a DEAE-Sepharose column equilibrated in 5 mM Tris pH 8.0 and the unbound fraction was collected, pooled and concentrated using an Amicon apparatus.

Antibody Adsorption: Affinity columns were produced by linking antigen to CNBR-Sepharose according to the Pharmacia protocol or by linking to controlled pore glass. The ratio of protein to resin for each column was as follows: 6 mg SHAM 3 per 1.5 g CPG, 10 mg $\alpha + \beta$ globulin per 2 g CNBR-Sepharose and 1 mg pdFVIII per 1 g CNBR-Sepharose. Following coupling, each resin was poured into a 1 × 10 cm column. All chromatography steps were performed with the assistance of a Pharmacia FPLC system. Resin was first equilibrated in 0.5M NaCl, 20 mM Tris, pH 7.5 (TBS), then sample was applied at a flow rate of 0.1 mL/min (7.6 mL cm $^{-2}$hr$^{-1}$). The column was washed with TBS until the absorbance at 280 nm returned to baseline at which time the direction of buffer flow through the column was reversed. The flow rate was increased to 0.25 mL/min (19.0mL cm $^{-2}$hr$^{-1}$) and the column was washed again until the absorbance returned to baseline. The column eluant collected to this point was pooled and concentrated to 3 to 5 mL using an Amicon concentrator. This fraction was either reapplied to the affinity column or saved for further analysis and it is referred to as the "Flow Through" fraction. To elute bound antibody, the column was washed with 1 M propionic acid in TBS until the absorbance at 280 nm reached a stable value. Prior to reapplication of sample, the column was washed with TBS until the pH returned to 7.5.

Electrophoretic Procedures: SDS-PAGE was performed on reduced, denatured samples using 4 to 12% acrylamide gradient gels according to Laemli; all procedures were carried out at room temperature. Gels were silver stained (Morrissey, 1981), or they were transferred electrophoretically overnight to nitrocellulose filters for Western immunoblotting (Towbin, 1984). Filters were blocked with 2% non-fat dry milk in TBS for 2 hours, then were probed with 10 mL of 5 $\mu$g/mL antibody in 2% milk in TBS. Filters were washed 3 times with 0.05% Tween 20 in TBS (TTBS) for 10 minutes, incubated for 2 hours with goat anti-rabbit antibody conjugated to horseradish peroxidase (Biorad) diluted 1:1000 with 2% milk in TBS, washed as above and stained according to the manufacturer's instructions.

Assays: Dot blot immunoassay was performed by spotting 1 $\mu$L (64 ng) antigen onto a nitrocellulose membrane that had been prewet with TBS and allowed to dry. Antigen was diluted in SDS-sample buffer and boiled for 3 minutes (denatured) or it was diluted in TBS (native). After air drying, the membrane was incubated for 1 hour at room temperature in 5% milk in TBS with shaking. The membrane was then washed 3 times with distilled water and 3 times with TTBS using 5 minute washing steps. The membrane was again airdried, spotted with 1 $\mu$L of serial dilutions of antibodies to be tested (diluted with 20 mM Tris, pH 8, 0.5 M NaCl, 0.5% Tween 80, 0.01% Thimerosal) and air-dried again. Membrane was then incubated 2 hours with goat anti-rabbit antibody conjugated to alkaline phosphatase (Biorad) diluted 1:5000 in 5% milk in TBS and washed 1 time with water, 3 times with TTBS and 2 times with TBS, using 5 minute washing steps. Alkaline phosphatase assays were performed by cutting the membrane into squares containing a single dot, then incubating each 1 cm square in 0.5 mL of 1 mg/mL p-nitrophenyl phosphate, 0.1 M Tris, 1 mM MgCl$_2$, pH 8.8 for 16 to 18 hours at room temperature. Samples were then pipetted into microtiter plate wells and the absorbance at 410 nm was determined with the aid of an MR 600 Dynatech micro-plate reader. Background signal obtained in the absence of antigen was subtracted from each assay value.

Protein was measured by the Pierce BCA assay kit according to the manufacturer's instructions.

Experimental

R$\alpha$rFVIII (20 mg) was passed 5 times over SHAM 3 conjugated to CPG, then 5 times over $\alpha+\beta$ globulin conjugated to Sepharose. See Table 1.

TABLE 1

| ANTIBODY ADSORPTION: NUMBER OF PASSES OVER EACH AFFINITY COLUMN | | | | |
|---|---|---|---|---|
| AFFINITY COLUMN | | ANTIBODY REFERENCE NUMBER | | |
| Antigen | mg | 3712-38 | 3712-39 | 3712-52 |
| SHAM 3 | 6 mg | 5 | 5 | 5 |
| $\alpha + \beta$ Globulin | 10 mg | | 5 | 5 |
| pdFVIII | 1 mg | | | 12 |

The resulting antibody (3712-39) did not cross-react with either SHAM 3 or $\alpha+\beta$ globulin when analyzed by a Western immunoblotting procedure, shown in FIG. 3. This is shown in FIG. 3, panel 1. Lane 1, pd, is pd FVIII; r is rFVIII; CSA is chicken serum albumin. When probed with antiserum 3712-39, antibodies to rFVIII, pdFVIII and CSA (with which the rabbits were also immunized) produced detectable bands against their respective antigens. To remove R$\alpha$FVIII antibody capable of cross-reacting with pdFVIII, the reference product in this example, antibody 3712-39 was passed 12 times over pdFVIII conjugated to Sepharose. Western immunoblot analysis of the resulting antibody (3712-52) indicated that all antibody capable of cross-reacting with pdFVIII had been adsorbed. As shown in FIG. 3, panel 3, the adsorbed antiserum did not react with pdFVIII (pd) or rFVIII (r). A CSA band is visualized, however, This indicates that all antibody capable of recognizing rFVIII was adsorbed by pdFVIII.

Although the rabbits immunized with rFVIII were also immunized with chicken serum albumin (CSA), antibody to this protein (3712-52) was not removed during the affinity chromatography steps (FIG. 3), indicating that FVIII antibody adsorption was specific.

A variation of the standard dot blot immunoassay was also used in this study in order to quantify the FVIII-specific antibody remaining after pdFVIII adsorption (Table 2).

TABLE 2

| | QUANTITATIVE DOT BLOT | |
|---|---|---|
| ANTIGEN | | ANTIBODY DETECTED IN FLOW-THROUGH FRACTION (% UNFRACTIONATED ± SD) |
| Denatured | pdFVIII | 3.1 ± 5.3 |
| | rFVIII | 4.9 ± 4.1 |
| Native | pdFVIII | 7.9 ± 3.8 |
| | rFVIII | 5.0 ± 2.9 |

This assay is similar to a reverse ELISA in that the antigen concentration remains constant while the antibody concentration is variable, allowing one to quantitate antibody specific for a given antigen. Analysis of antibody before and after pdFVIII adsorption using denatured pdFVIII showed that the FVIII-specific antibody had been adsorbed. Similar results were seen for denatured rFVIII as well as for native pdFVIII and rFVIII.

Recovery of IgG through the adsorption steps as measured by total protein is shown in Table 3. Although approximately 90% of the antibody was recovered after each cycle, the large number of passes required for complete antibody removal resulted in low recovery values.

TABLE 3

| ANTIBODY RECOVERY AFTER EACH AFFINITY COLUMN | |
|---|---|
| COLUMN | PROTEIN RECOVERED % TOTAL |
| SHAM 3 | 87 |
| $\alpha + \beta$ Globulin | 56 |
| pdFVIII | 18 |

In this example, antibody was raised to rFVIII and tested for the presence of antibody that would recognize rFVIII, but not pdFVIII. This putative rFVIII-specific antibody should not bind to a pdFVIII affinity column, therefore, after removing antibody directed to non-FVIII protein, animal antibody was contacted with pdFVIII by adsorption with pdFVIII conjugated to Sepharose. Western immunoblot analysis showed that adsorption removed all antibody capable of recognizing pdFVIII as well as that capable of recognizing rFVIII (FIG. 3), indicating that no rFVIII-specific antibody could be detected. Antibody adsorbed with pdFVIII was also analyzed by dot blot immunoassay. When either denatured or native, rFVIII or pdFVIII was used as the capture antigen, native antigens gave slightly higher values than denatured antigens, but there was not a significant difference in the values obtained for rFVIII compared to pdFVIII, showing that rFVIII-specific antibody was not detected (Table 2). The lack of such antibody is consistent with the notion that rFVIII does not contain unique epitopes compared to pdFVIII.

There are several assumptions built into this immunogenicity test system that need to be clarified. First of all, it is assumed that epitopes distinguished by the human immune system will be detected by the rabbit immune system. Other reference animals may be used in appropriate circumstances in the evaluation of other products. Also, relevant conformational epitopes on the product to be evaluated must not be destroyed by the procedure used to immunize the animal. Evidence that R$\alpha$rFVIII recognizes many rFVIII epitopes comes from our characterization of the antibody. R$\alpha$rFVIII is neutralizing and is capable of detecting all polypeptides recognized by any monoclonal or polyclonal antibody we have evaluated (including antibody from FVIII inhibitor patients), especially in ELISA systems for which it serves as a capture antibody. To increase the chance that antibody would be raised to all epitopes, three rabbits were immunized with rFVIII and adsorption studies were performed on a pool of sera from these animals. This should have optimized the yield of antibody directed against all possible rFVIII epitopes. A final assumption is that epitope-specific antibody will be detected by our assay systems. Our initial assay system, Western blot analysis, was chosen because it provided a sensitive antibody assay and allowed for characterization of antibody specificity. Dot blot immunoassay was also used because it allowed quantitation of the FVIII-specific antibody remaining after adsorption and it permitted testing for antibody recognizing native FVIII conformational epitopes. By using such detection systems, the ability to detect unique epitope-specific antibody should have been maximized.

In the present practice of this invention, multiple passes over each affinity column are required for complete antibody adsorption. Both SHAM 3 and $\alpha+\beta$ globulin columns required 5 cycles for complete adsorption, while pdFVIII required 12 cycles. Since the pdFVIII affinity column contains less protein per unit resin than either the SHAM 3 or the $\alpha+\beta$ globulin columns (Table 1), this is to be expected. The large number of cycles caused the final antibody yield to be quite low (Table 2). However, apparent adsorption of FVIII-specific antibody can not be attributed to low antibody yields, since pdFVIII adsorbed antibody (3712-52) still retained ability to react with chicken albumin (FIG. 2).

There are few established methodologies designed to explore the potential immunogenicity of a recombinant protein. The present invention circumvents this problem and allows prediction of protein immunogenicity.

REFERENCES

Pannell, R., Johnson, D. and Travis, J. 1974; Biochemistry 13:5439-5445.

Rosenberg, S., Barr, P. J., Najarian, R. C. and Hallewell, R. A. 1984; Synthesis in yeast of a functional oxidation-resistant mutant of human Alpha-1 Nature 312:77-80.

Courtney, M., Buchwalder, A., Tessier, L. H., Jaye, M., Benavente, A., Balland, A., Kohli, V., Lathe, R., Tolstoshev, P. and Lecocq, J. P., 1984; High-level production of biologically active human Alpha-1-antitrypsin in *Escherichia coli*. Proc. Nat. Acad. Sci. 81:669-673.

Courtney, M., Jallat, S., Tessier, L. H., Benavente, A., Crystal, R. G. and Lecocq, J. P. 1985; Synthesis in *E. coli* of Alpha-1-antitrypsin variants of therapeutic potential for emphysema and thrombosis. Nature 313:149-151.

Travis, J., Rosenberg, S., Barr, P., Hallewell, R., Owen, M., George, P. and Carrell, R. 1985; Isolation and properties of human Alpha-1-Proteinase Inhibitor variants produced in yeast. J. Biol. Chem 260:4384-4389.

Janoff, A., George-Nascimento, C. and Rosenberg, S. 1986; A genetically engineered mutant human Alpha-1-Proteinase-Inhibitor is more resistant then the normal inhibitor to oxidative inactivation by chemicals, enzymes, cell and cigarette smoke. Am. Rev. Respir. Dis. 133:400-408.

Coan, M. H., Brockway, W. J., Equizabel, A., Kreig, T. and Fournel, M. A. 1985; Preparation and properties of Alpha-1-Proteinase Inhibitor concentrate from human plasma. Vox Sang 48:333-342.

Glaser, C. B., Chamomorro, M., Crowley, R., Karic, L. J., Childes, A. and Calderon, M. 1982; The isolation of Alpha-1-proteinase inhibitor by a unique procedure designed for industrial application. Analytical Biochemistry 124:364-371.

Revak, S. D., Rice, C. L., Schraufstatter, I. U., Halsey, Jr., W. A., Bohl, B. P., Clancy, R. M. and Cochrane, C. G. 1985; Experimental pulmonary inflammatory injury in the monkey. J. Clin. Inves. 76:1182-1192.

Li Laemmli, U. K. 1970; Cleavage of structural proteins during the assembly of the head of bacteriophage T4 Nature 227:680-685.

Morrissey, J. H. 1981; Silver stain for proteins in polyacrylamide gels: a modified procedure with enhanced uniform sensitivity. Analytical Biochemistry 117:307-310.

Ovary, Z., 1958; Prog. Allergy 5:459-508.

Renart, J., Reiser R. and Stark, G. R. 1979. Transfer of proteins from gels to DMB paper and detection with antisera: a method for studying antibody specificity and structure. Proc. Nat. Acad. Sci. 76:3116.

Gervoy, J. S., et al, 1977; Methods in Immunol. 445-458.

Sharon, N. 1980; Carbohydrates. Sci Amer. 243:90-116.

Towbin, H. and Gordon, J. 1981; J. Immunol. Meth. 72:313-340.

We claim:

1. A method of evaluating the immunogenicity of a first product (PX) that is a recombinant product in comparison to a reference produce (PR) which is the naturally-occurring equivalent of the first product, comprising:
   (a) administering PX to an animal to produce antibodies to PX;
   (b) contacting said antibodies with PR to remove antibody to PR from said antibodies, thereby producing a depleted antibody preparation; and
   (c) reacting said depleted antibody preparations with PX, whereby the detection of the presence of antibodies capable of recognizing PX is indicative of a potential immunogenic reaction in humans.

2. The method of claim 1 wherein said animal is a New Zealand white rabbit.

3. The method of claim 1 wherein said administering PX further comprises the step of using an adjuvant.

4. The method of claim wherein said PX is a protein produced from recombinant DNA and said PR is a protein derived from the group consisting of human plasma, tissue and urine.

5. The method of claim 1 wherein said contacting of said depleted antibody preparation further comprises coupling PR to a solid support.

6. The method of claim 5 wherein said solid support is an agarose column and said coupling is done with cyanogen bromide.

7. The method of claim 1 wherein reacting of said depleted antibody preparation is carried out by Western immunoblot analysis membrane.

8. A method of evaluating the potential for immunological reaction in humans of a protein PX that is a recombinant product in comparison to a reference product (PR) which is the naturally-occurring equivalent of the first product, comprising:
   (a) raising antibodies to PX in an animal;
   (b) isolating said antibodies in an antibody preparation;
   (c) removing from said antibody preparation, by affinity chromatography, any and all antibodies to PR to produce a depleted antibody preparation; and
   (d) reacting said depleted antibody preparation with PR and PX, whereby a positive reaction with PX and not with PR indicates that PX elicits antibody not recognizing PR thereby indicating that PX can potentially cause an immunological reaction in humans.

* * * * *